(12) United States Patent
Lubisch et al.

(10) Patent No.: US 6,277,850 B1
(45) Date of Patent: Aug. 21, 2001

(54) PYRROLYL QUINOXALINDIONES THEIR PRODUCTION AND USE AS AMPA RECEPTOR ANTAGONISTS

(75) Inventors: Wilfried Lubisch, Mannheim; Berthold Behl; Hans-Peter Hofmann, both of Limburgerhof; Laszlo Szabo, Dossenheim, all of (DE)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/202,153

(22) PCT Filed: Jun. 5, 1997

(86) PCT No.: PCT/EP97/02913

§ 371 Date: Dec. 9, 1998

§ 102(e) Date: Dec. 9, 1998

(87) PCT Pub. No.: WO97/49701

PCT Pub. Date: Dec. 31, 1997

(30) Foreign Application Priority Data

Jun. 21, 1996 (DE) .............................. 196 24 808

(51) Int. Cl.⁷ ........................ A61K 31/498; C07D 403/10
(52) U.S. Cl. ............................... 514/249; 544/354
(58) Field of Search ............................. 544/354; 514/249

(56) References Cited

U.S. PATENT DOCUMENTS 5,714,489   2/1998   Lubisch et al. ..................... 514/249

FOREIGN PATENT DOCUMENTS

| 2099270 | 4/1993 | (CA) . |
| 41 35 871 | 4/1993 | (DE) . |
| 43 40 045 | 6/1995 | (DE) . |
| 260 467 | 3/1988 | (EP) . |
| 315 959 | 5/1989 | (EP) . |
| 374 534 | 6/1990 | (EP) . |
| 377 112 | 7/1990 | (EP) . |
| 572 852 | 12/1993 | (EP) . |
| 91 13878 | 9/1991 | (WO) . |
| 92 07847 | 5/1992 | (WO) . |
| 95 35289 | 12/1995 | (WO) . |
| 96 19476 | 6/1996 | (WO) . |

OTHER PUBLICATIONS

Bio. Med. Chem. Tett. vol. 6, No. 23, 1996, 2886–92.
Lipton, *TINS*, vol. 16, No. 12, pp. 527–532, 1993.*
Lees, *Pharmacology and Pathophysiology*, pp. 51–74, 1996.*
Doble, *Therapie*, 50, pp. 319–337, 1995.*

* cited by examiner

*Primary Examiner*—Emily Bernhardt
(74) *Attorney, Agent, or Firm*—Keil & Weinkauf

(57) ABSTRACT

Pyrrolylquinoxalinediones of the formula I

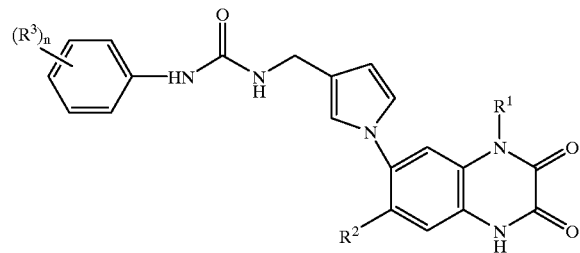

and their tautomeric and isomeric forms, and their physiologically tolerated salts are described, where the variables have the following meaning:

$R^1$ hydrogen, $C_1$–$C_6$-alkyl, substituted by hydroxyl or carboxyl, $R^2$ hydrogen, $C_1$–$C_6$-alkyl, $C_2$–$C_6$-alkenyl, $C_2$–$C_6$-alkynyl, a chlorine, fluorine or bromine atom, a trihalomethyl, cyano or nitro group or $SO_2$—$C_1$–$C_4$-alkyl, $R^3$ COOH or a radical which can be hydrolyzed to the carboxyl group, n 1 or 2.

9 Claims, No Drawings

PYRROLYL QUINOXALINDIONES THEIR PRODUCTION AND USE AS AMPA RECEPTOR ANTAGONISTS

The present invention relates to pyrrolylquinoxalinediones of the formula I

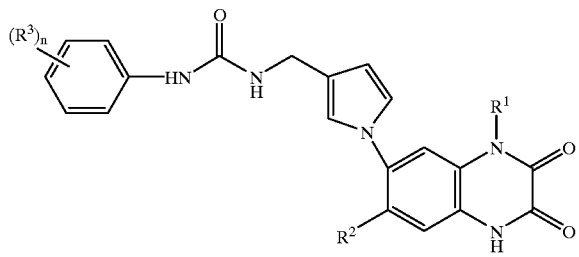

and their tautomeric and isomeric forms, and their physiologically tolerated salts, where the variables have the following meaning:

$R^1$ hydrogen, $C_1$–$C_6$-alkyl, substituted by hydroxyl or carboxyl, $R^2$ hydrogen, $C_1$–$C_6$-alkyl, $C_2$–$C_6$-alkenyl, $C_2$–$C_6$-alkynyl, a chlorine, fluorine or bromine atom, a trihalomethyl, cyano or nitro group or $SO_2$—$C_1$–$C_4$-alkyl, $R^3$ COOH or a radical which can be hydrolyzed to the carboxyl group, n 1 or 2.

The invention furthermore relates to processes for their preparation and to their use for controlling diseases.

Derivatives of quinoxaline-2,3(1H, 4H)-dione of the formula A

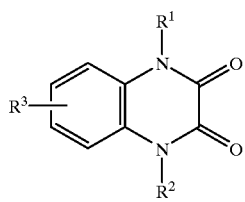

have been described in several publications, such as EP-A-374 534 and EP-A-260 467, as glutamate antagonists. Many known derivatives are unsubstituted in the heterocyclic quinoxaline fragment (A with $R^1$, $R^2$=hydrogen). Furthermore, derivatives in which $R^1$ in A is a radical which is not hydrogen are also known. Thus, EP-A-377 112 and EP-A-374 534 have disclosed N-hydroxyquinoxalines (A; $R^1$=$OR^4$). EP-A-315 959, DE-A-41 35 871, WO 91/13 878 and WO 92/07 847 describe alkyl radicals as $R^1$ in A, it also being possible for the alkyl chain to be substituted by acids, esters or amides.

Quinoxalinedione derivatives of the formula A which have a heterocycle as substituent $R^3$ are likewise known. Thus, EP-A-556 393 describes imidazoles, triazoles and pyrazoles. Quinoxalinedione derivatives having a pyrrolyl radical as $R^3$ are disclosed in EP-A-572 852 and WO 95/35 289. DE-A-43 400 45 mentions pyrrole derivatives which have a urea residue as glutamate antagonists.

The known pyrrolylquinoxalinedione compounds are still not always entirely satisfactory with regard to their pharmacological effect. It is an object of the present invention to provide pyrrolylquinoxalinedione derivatives with improved activity and, at the same time, good physiological tolerability.

We have found that this object is achieved by the pyrrolylquinoxalinediones of the formula I mentioned at the outset.

The radicals $R^1$–$R^3$ in formula I have the following meanings:

$R^1$ is hydrogen or branched or unbranched $C_1$–$C_6$-alkyl, substituted by hydroxyl or carboxyl, eg. hydroxyethyl or carboxymethyl. $C_1$–$C_6$-Alkyl is, for example, methyl, ethyl, propyl, isopropyl, butyl, sec-butyl, tert-butyl. In the case of the hydroxyl-substituted compounds, alkyl is preferably $C_2$–$C_6$-alkyl.

$R^2$ is hydrogen, $C_1$–$C_6$-alkyl, eg. as mentioned above, $C_2$–$C_6$-alkenyl or—alkynyl, eg. vinyl, ethynyl, propenyl, isopropenyl, fluorine, chlorine, bromine, trihalomethyl, eg. trichloromethyl or trifluoromethyl, cyano or nitro, and $SO_2$—$C_1$–$C_4$-alkyl, where the alkyl radical has the abovementioned meanings. Particularly preferred radicals $R^2$ are hydrogen, chlorine, trifluoromethyl or nitro.

$R^3$ is a carboxyl group COOH or a radical which can be hydrolyzed to the carboxyl group, eg. an amide group, a carboxylic anhydride group or, in particular, an ester group $COOR^4$ where $R^4$ is $C_1$–$C_4$-alkyl, eg. $COOCH_3$ or $COOC_2H_5$. In the case of two adjacent carboxyl groups, they may form a cyclic anhydride. Particularly preferred for the pharmacological effect is the free COOH group or its salts.

The variable n is 1 or 2, in particular 1.

The substituent(s) $R^3$ can be located in the position meta, para or ortho to the urea residue. The para and/or meta position is preferred.

Particularly preferred compounds are those where $R^1$ is hydrogen, $R^2$ is hydrogen, chlorine, a trifluoromethyl or nitro group, $R^3$ is COOH and n is 1 or 2.

Further particularly preferred compounds are those where $R^1$— is $CH_2COOH$ or —$CH_2CH_2OH$, $R^2$ is hydrogen, chlorine, a trifluoromethyl or nitro group, $R^3$ is COOH, and n is 1 or 2.

The compounds I according to the invention can be prepared as shown in reaction scheme 1.

Reaction scheme 1

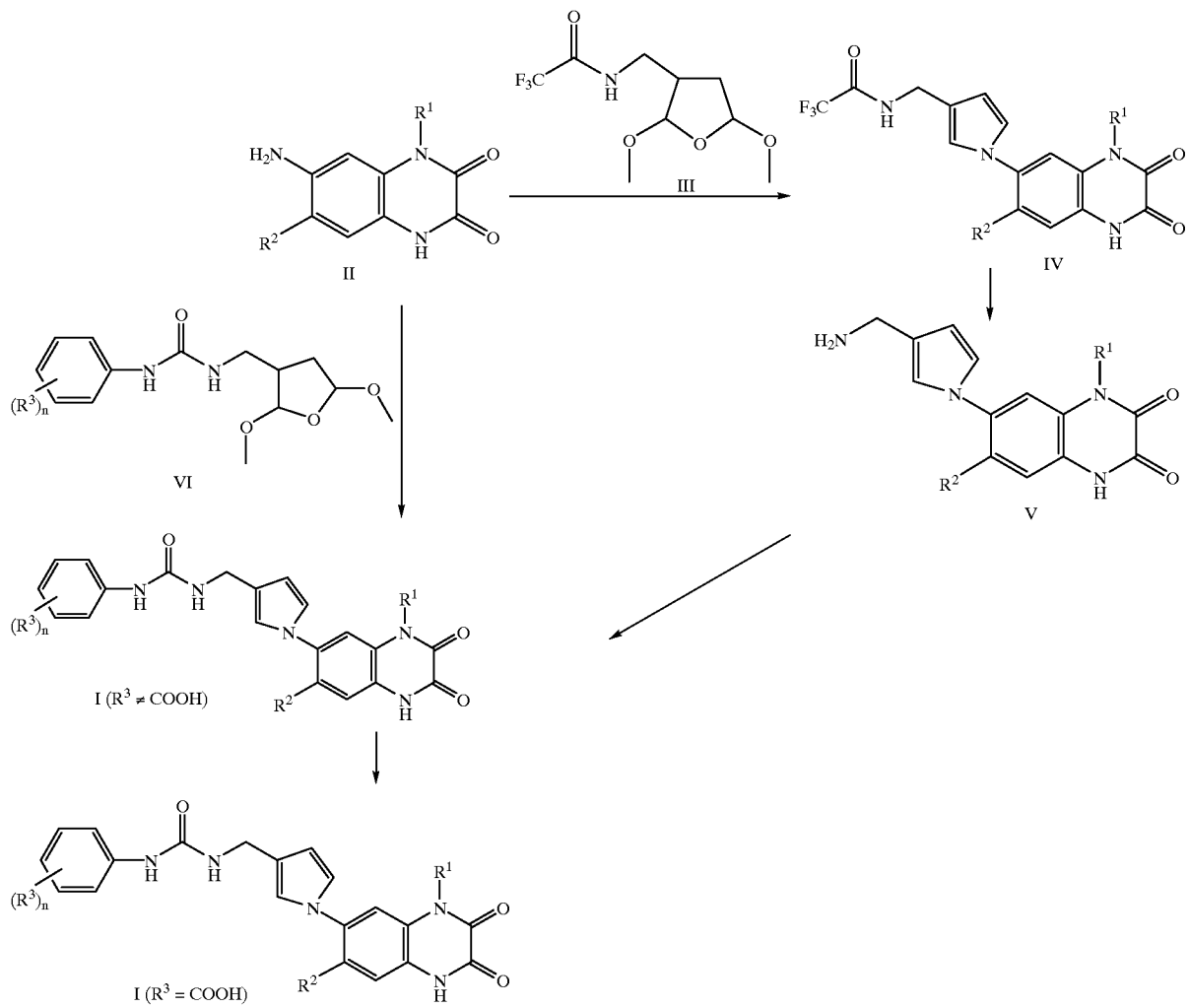

This entails amino-substituted oumnoxalinediones of the formula II being reacted with a 1,4-dicarbonyl compound or cyclic acetals derived therefrom (III and VI) with elimination of water to give the pyrroles I and IV. The processes used for this are the conventional ones described, for example, in A. R. Katritzky and C. W. Rees, "Comprehensive Heterocyclic Chemistry", Vol.4, Part 306, pages 313 et seq., in C. Ferri, "Reaktionen der organischen Synthese", Thieme Verlag 1978, pages 708 et seq., or in EP-A-572 852 and DE-A-43 400 45. The pyrrole synthesis is normally catalyzed by acid and takes place in the presence of acetic acid or toluenesulfonic acid. The acid can also act as solvent if used in larger amounts. However, it is generally customary to carry out the reaction in a solvent such as toluene or in a mixture of solvents such as toluene/dimethylformamide at from 50 to 150° C., preferably 100 to 150° C., or in concentrated acetic acid at from 50° C. to the boiling point.

If the dicarbonyl compound employed, for example compound III in scheme 1, has an amino group, this is protected beforehand. Known protective groups such as amides, urethanes or benzyl radicals can be employed, and trifluoroacetyl is preferably used. Other possible protective groups and introduction methods are indicated in Th. W. Green and P. G. M. Wuts, "Protective Groups in Organic Synthesism", Wiley&Sons 1991, Chapter 7. The protective groups are removed in a conventional way after the pyrrole ring has been synthesized, resulting in the amine V. Elimination of the amide protective group preferably takes place with acids or bases such as lithium hydroxide in a solvent or solvent mixtures such as tetrahydrofuran/water at from 10 to 60° C., preferably 20 to 30° C.

The amines of the formula V can then be reacted in a conventional way with isocyanates to give the compounds of the formula I according to the invention, it also being possible to use in place of the isosocyanate the corresponding anilines which, in this case, are reacted in a known manner with phosgene or analogous compounds, such as carbonyl diimidazole, to give the isocyanates in situ. These and similar processes are described, for example, in Houben-Weyl, "Methoden der organischen Chemier", Vol. E4, pages 334 et seq.

In place of the amide III, it is also possible to employ the corresponding aldehyde which is subsequently converted, in a reductive amination, into the amines V.

The pyrrolylquinoxalinediones according to the invention can be obtained directly by starting from the aniline compounds II and using the acetals VI. The procedure for this is similar to that for preparing the pyrroles V.

The ester in the urea derivative I can be converted into the corresponding acid with acids or bases. This preferably takes place with bases such as lithium hydroxide in solvent mixtures such as tetrahydrofuran/water at 20 to 30° C.

The compounds according to the invention which are mentioned by way of example in the table can be prepared by the abovementioned synthetic route:

TABLE 1

I $R^3$ = COOH

| $R^1$ | $R^2$ | n | Position |
|---|---|---|---|
| $CH_2CH_2OH$ | H | 1 | para |
| $CH_2CH_2OH$ | H | 1 | meta |
| $CH_2CH_2OH$ | H | 1 | ortho |
| $CH_2CH_2OH$ | Cl | 1 | para |
| $CH_2CH_2OH$ | Cl | 1 | meta |
| $CH_2CH_2OH$ | Cl | 1 | ortho |
| $CH_2CH_2OH$ | $CF_3$ | 1 | para |
| $CH_2CH_2OH$ | $CF_3$ | 1 | meta |
| $CH_2CH_2OH$ | $CF_3$ | 1 | ortho |
| $CH_2CH_2OH$ | $NO_2$ | 1 | para |
| $CH_2CH_2OH$ | $NO_2$ | 1 | meta |
| $CH_2CH_2OH$ | $NO_2$ | 1 | ortho |
| $CH_2CH_2OH$ | H | 2 | para/meta |
| $CH_2CH_2OH$ | Cl | 2 | para/meta |
| $CH_2CH_2OH$ | $CF_3$ | 2 | para/meta |
| $CH_2CH_2OH$ | $NO_2$ | 2 | para/meta |
| $CH_2CH(OH)CH_3$ | H | 1 | para |
| $CH_2CH(OH)CH_3$ | H | 1 | meta |
| $CH_2CH(OH)CH_3$ | Cl | 1 | para |
| $CH_2CH(OH)CH_3$ | Cl | 1 | meta |
| $CH_2CH(OH)CH_3$ | $CF_3$ | 1 | para |
| $CH_2CH(OH)CH_3$ | $CF_3$ | 1 | meta |
| $CH_2CH(OH)CH_3$ | $NO_2$ | 1 | para |
| $CH_2CH(OH)CH_3$ | $NO_2$ | 1 | meta |
| $CH_2CH(OH)CH_3$ | H | 2 | para/meta |
| $CH_2CH(OH)CH_3$ | Cl | 2 | para/meta |
| $CH_2CH(OH)CH_3$ | $CF_3$ | 2 | para/meta |
| $CH_2CH(OH)CH_3$ | $NO_2$ | 2 | para/meta |
| $CH_2CH_2CH_2OH$ | H | 1 | para |
| $CH_2CH_2CH_2OH$ | H | 1 | meta |
| $CH_2CH_2CH_2OH$ | Cl | 1 | para |
| $CH_2CH_2CH_2OH$ | Cl | 1 | meta |
| $CH_2CH_2CH_2OH$ | $CF_3$ | 1 | para |
| $CH_2CH_2CH_2OH$ | $CF_3$ | 1 | meta |
| $CH_2CH_2CH_2OH$ | $NO_2$ | 1 | para |
| $CH_2CH_2CH_2OH$ | $NO_2$ | 1 | meta |
| $CH_2CH_2CH_2OH$ | H | 2 | para/meta |
| $CH_2CH_2CH_2OH$ | Cl | 2 | para/meta |
| $CH_2CH_2CH_2OH$ | $CF_3$ | 2 | para/meta |
| $CH_2CH_2CH_2OH$ | $NO_2$ | 2 | para/meta |
| $CH_2CH(OH)CH_2CH_3$ | H | 1 | para |
| $CH_2CH(OH)CH_2CH_3$ | H | 1 | meta |
| $CH_2CH(OH)CH_2CH_3$ | Cl | 1 | para |
| $CH_2CH(OH)CH_2CH_3$ | Cl | 1 | meta |
| $CH_2CH(OH)CH_2CH_3$ | $CF_3$ | 1 | para |
| $CH_2CH(OH)CH_2CH_3$ | $CF_3$ | 1 | meta |
| $CH_2CH(OH)CH_2CH_3$ | $NO_2$ | 1 | para |
| $CH_2CH(OH)CH_2CH_3$ | $NO_2$ | 1 | meta |
| $CH_2CH(OH)CH_2CH_3$ | H | 2 | para/meta |
| $CH_2CH(OH)CH_2CH_3$ | Cl | 2 | para/meta |
| $CH_2CH(OH)CH_2CH_3$ | $CF_3$ | 2 | para/meta |
| $CH_2CH(OH)CH_2CH_3$ | $NO_2$ | 2 | para/meta |
| $CH_2CH_2CH(OH)CH_3$ | H | 1 | para |
| $CH_2CH_2CH(OH)CH_3$ | H | 1 | meta |
| $CH_2CH_2CH(OH)CH_3$ | Cl | 1 | para |
| $CH_2CH_2CH(OH)CH_3$ | Cl | 1 | meta |
| $CH_2CH_2CH(OH)CH_3$ | $CF_3$ | 1 | para |
| $CH_2CH_2CH(OH)CH_3$ | $CF_3$ | 1 | meta |
| $CH_2CH_2CH(OH)CH_3$ | $NO_2$ | 1 | para |
| $CH_2CH_2CH(OH)CH_3$ | $NO_2$ | 1 | meta |
| $CH_2CH_2CH(CH)CH_3$ | H | 2 | para/meta |
| $CH_2CH_2CH(OH)CH_3$ | Cl | 2 | para/meta |
| $CH_2CH_2CH(OH)CH_3$ | $CF_3$ | 2 | para/meta |
| $CH_2CH_2CH(OH)CH_3$ | $NO_2$ | 2 | para/meta |
| $(CH_2)_4OH$ | H | 1 | para |
| $(CH_2)_4OH$ | H | 1 | meta |

TABLE 1-continued

I $R^3 = COOH$

| $R^1$ | $R^2$ | n | Position |
|---|---|---|---|
| (CH$_2$)$_4$OH | Cl | 1 | para |
| (CH$_2$)$_4$OH | Cl | 1 | meta |
| (CH$_2$)$_4$OH | CF$_3$ | 1 | para |
| (CH$_2$)$_4$OH | CF$_3$ | 1 | meta |
| (CH$_2$)$_4$OH | NO$_2$ | 1 | para |
| (CH$_2$)$_4$OH | NO$_2$ | 1 | meta |
| (CH$_2$)$_4$OH | H | 2 | para/meta |
| (CH$_2$)$_4$OH | Cl | 2 | para/meta |
| (CH$_2$)$_4$OH | CF$_3$ | 2 | para/meta |
| (CH$_2$)$_4$OH | NO$_2$ | 2 | para/meta |
| (CH$_2$)$_6$OH | H | 1 | para |
| (CH$_2$)$_6$OH | H | 1 | meta |
| (CH$_2$)$_6$OH | Cl | 1 | para |
| (CH$_2$)$_6$OH | Cl | 1 | meta |
| (CH$_2$)$_6$OH | CF$_3$ | 1 | para |
| (CH$_2$)$_6$OH | CF$_3$ | 1 | meta |
| (CH$_2$)$_6$OH | NO$_2$ | 1 | para |
| (CH$_2$)$_6$OH | NO$_2$ | 1 | meta |
| (CH$_2$)$_6$OH | H | 2 | para/meta |
| (CH$_2$)$_6$OH | Cl | 2 | para/meta |
| (CH$_2$)$_6$OH | CF$_3$ | 2 | para/meta |
| (CH$_2$)$_6$OH | NO$_2$ | 2 | para/meta |
| CH$_2$COOH | H | 1 | para |
| CH$_2$COOH | H | 1 | meta |
| CH$_2$COOH | H | 1 | ortho |
| CH$_2$COOH | Cl | 1 | para |
| CH$_2$COOH | Cl | 1 | meta |
| CH$_2$COOH | Cl | 1 | ortho |
| CH$_2$COOH | CF$_3$ | 1 | para |
| CH$_2$COOH | CF$_3$ | 1 | meta |
| CH$_2$COOH | CF$_3$ | 1 | ortho |
| CH$_2$COOH | NO$_2$ | 1 | para |
| CH$_2$COOH | NO$_2$ | 1 | meta |
| CH$_2$COOH | NO$_2$ | 1 | ortho |
| CH$_2$COOH | H | 2 | para/meta |
| CH$_2$COOH | Cl | 2 | para/meta |
| CH$_2$COOH | CF$_3$ | 2 | para/meta |
| CH$_2$COOH | NO$_2$ | 2 | para/meta |
| CH$_2$CH$_2$COOH | H | 1 | para |
| CH$_2$CH$_2$COOH | H | 1 | meta |
| CH$_2$CH$_2$COOH | Cl | 1 | para |
| CH$_2$CH$_2$COOH | Cl | 1 | meta |
| CH$_2$CH$_2$COOH | CF$_3$ | 1 | para |
| CH$_2$CH$_2$COOH | CF$_3$ | 1 | meta |
| CH$_2$CH$_2$COOH | NO$_2$ | 1 | para |
| CH$_2$CH$_2$COOH | NO$_2$ | 1 | meta |
| CH$_2$CH$_2$COOH | H | 2 | para/meta |
| CH$_2$CH$_2$COOH | Cl | 2 | para/meta |
| CH$_2$CH$_2$COOH | CF$_3$ | 2 | para/meta |
| CH$_2$CH$_2$COOH | NO$_2$ | 2 | para/meta |
| (CH$_2$)$_3$COOH | H | 1 | para |
| (CH$_2$)$_3$COOH | H | 1 | meta |
| (CH$_2$)$_3$COOH | Cl | 1 | para |
| (CH$_2$)$_3$COOH | Cl | 1 | meta |
| (CH$_2$)$_3$COOH | CF$_3$ | 1 | para |
| (CH$_2$)$_3$COOH | CF$_3$ | 1 | meta |
| (CH$_2$)$_3$COOH | NO$_2$ | 1 | para |
| (CH$_2$)$_3$COOH | NO$_2$ | 1 | meta |
| (CH$_2$)$_3$COOH | H | 2 | para/meta |
| (CH$_2$)$_3$COOH | Cl | 2 | para/meta |
| (CH$_2$)$_3$COOH | CF$_3$ | 2 | para/meta |
| (CH$_2$)$_3$COOH | NO$_2$ | 2 | para/meta |

The compounds according to the invention are antagonists of the excitatory amino acid glutamate, in particular antagonists of the glycine-binding site of the NMDA receptor (NMDA=N-methyl-D-aspartate), of the AMPA receptor (AMPA=2-amino-3-hydroxy-5-methyl-4-isoxazolepropionic acid) and of the kainate receptor.

Glutamate activity is elevated in a number of neurological disorders or psychological disturbances, and this leads to states of overexcitation or toxic effects in the central nervous system (CNS).

Antagonists to the glutamate receptor subtypes can thus be employed for treating these disorders. Glutamate antagonists, which include, in particular, NMDA antagonists and their modulators (such as glycine antagonists) and the AMPA antagonists, are suitable for therapeutic use for neurodegenerative disorders (Huntington's chorea and Parkinson's disease), neurotoxic disturbances after hypoxia, anoxia or ischemia, as occur after a stroke, or else as antiepileptics, antidepressants and anxiolytics (cf. Arzneim. Forschung 40 (1990) 511–514; TIPS 11 (1990) 334–338 and Drugs of the Future 14 (1989) 1059–1071).

The pharmacological effect of the compounds I has been investigated on membrane material isolated from rat cerebra. For this purpose, the membrane material was treated in the presence of the compounds according to the invention with the radio labeled substances $^3$H-2-amino-3-hydroxy-5-methyl-4-isoxazolepropionic acid ($^3$H-AMPA), [$^3$H]-glycine or [$^3$H]-kainate, the latter binding to specific receptors (AMPA, NMDA or kainate receptors). The radioactivity on the treated membranes was then measured by scintillation counting. The amounts of bound $^3$H-AMPA, [$^3$H]-glycine or [$^3$H]-kainate, or in each case the amounts of these radio labeled substances displaced, can be determined from the bound radioactivity. The method is similar to that of T. Honore et al., Science 241 (1988) 701–703.

The dissociation constant $K_I$ (I=inhibitor) which results from this and which is a measure of the displacing effect of the agent according to the invention was found by iterative non-linear regression analysis using the statistical analysis system (SAS) on an IBM computer, similar to the "Ligand" program of P. J. Munson and D. Rodbard (Analytical Biochem. 107 (1980) 220, Ligand: Versatile Computerized Approach for Characterization of Ligand Bindung Systems).

The following in vitro investigations have been carried out:

1. Binding of $^3$H-2-amino-3-hydroxy-5-methyl-4-isoxazolepropionic acid($^3$H-AMPA).

The membrane material was prepared by homogenizing freshly removed rat cerebra together with 15 times the volume of a buffer solution A consisting of 30 mM tris (hydroxymethyl)methylamine hydrochloride (TRIS-HCl) and 0.5 mM ethylenediaminetetraacetic acid (EDTA), pH 7.4, using an Ultra-Turrax. The suspension was centrifuged at 48000 g for 20 min. After removal of the supernatant liquid, the proteinaceous membrane material present in the sediment was washed three times by suspending in buffer solution A and subsequently centrifuging at 48000 g for 20 minutes each time. The membrane material was then suspended in 15 times the volume of buffer solution A and incubated at 37° C. for 30 min. The protein material was subsequently washed twice by centrifugation and suspension and stored at –70° C. until used.

For the binding assay, the protein material was thawed at 37° C. and washed twice by centrifugation at 48000 g (20 min) and subsequent suspension in a buffer solution B consisting of 50 mM TRIS-HCl, 0.1 M potassium thiocyanate and 2.5 mM calcium chloride, pH 7.1. Subsequently, 0.25 mg of membrane material, 0.1 μCi of $^3$H-AMPA (60 Ci/mmol) and compound I were dissolved in 1 ml of buffer solution B and incubated on ice for 60 min. The incubated solution was filtered through a CF/B filter (Whatman) which had previously been treated for at least 2 hours with a 0.5% strength aqueous solution of polyethyleneimine.

The membrane residue was subsequently washed with 5 ml of cold buffer solution B in order to separate bound and free $^3$H-AMPA from one another. After measurement of the radioactivity of the bound $^3$H-AMPA in the membrane material by scintillation counting, the $K_I$ was determined by regression analysis of the displacement plots.

The $K_I$ found for N-(1-(6-trifluoromethylquinoxaline-2,3 (1H, 4H)-dion-7-yl)pyrrol-3-ylmethyl)-N'-(4-carboxyphenyl)urea (Example 2) was <10 M. The substance is accordingly distinctly more active than the urea derivative which is unsubstituted in the phenyl ring and is mentioned as Example 4 in DE-A-43 400 45.

2. Binding of [$^3$H]-glycine

The membranes were prepared for the $^3$H-glycine binding assay by homogenizing freshly removed rat hippocampi in 10 times the volume of preparation buffer (50 mM Tris-HCl, 10 mM EDTA) using a Potter homogenizer. The homogenate was centrifuged at 48000 g for 20 min. The supernatant was discarded and the membranes present in the pellet were washed 2× by resuspension and centrifugation at 48000 g (20 min each time). The resuspended membranes were frozen in liquid nitrogen and thawed again at 37° C. After another washing step, the membrane suspension was incubated in a shaking water bath at 37° C. for 15 min. After 4 more washing steps (centrifugation at 48000 g for 20 min each time and resuspension in preparation buffer), the membranes were stored at –70° C. until used further.

The frozen membranes were thawed at 37° C. and washed 2× by centrifugation at 48000 g (20 min) followed by resuspension in binding buffer (50 mM Tris-HCl pH 7.4, 10 mM MgCl$_2$). An incubation mixture contained 0.25 mg of protein (membranes), 25 nM $^3$H-glycine (16 Ci/mmol) and the substances to be tested in a total of 0.5 ml of binding buffer. The nonspecific binding was determined by adding 1 mM glycine.

Incubation at 4° C. for 60 min. was followed by filtration through GF/B filters and subsequent washing with about 5 ml of ice-cold binding buffer to separate bound and free ligand from one another. The radioactivity remaining on the filters was determined by liquid scintillation counting. The dissociation constants were calculated from the displacement plots using an iterative nonlinear fitting program or in accordance with the equation of Cheng and Prusoff (Biochem. Pharmacol. 22 (1993) 3099).

3. Binding of [$^3$H]-kainate

Membranes were prepared for the [$^3$H]-kainate binding assay by homogenizing freshly removed rat cerebra in 15 times the volume of preparation buffer (30 mM Tris-HCl—pH 7.4–0.5 mM EDTA) using an Ultra-Turrax$^R$. The homogenate was centrifuged at 48000 g for 20 min. The supernatant was discarded and the membranes present in the pellet were washed a total of 3× by resuspension in preparation buffer and centrifugation at 48000 g (20 min. each time). After the third washing step, the membranes were stored at –70° C. until used further.

The frozen membranes were thawed at 37° C., suspended in binding buffer (50 mM Tris-HCl, pH 7.4) and centrifuged at 48000 g for 20 min. The membranes present in the pellet were resuspended in binding buffer. One incubation mixture contained 0.25 mg of protein (membranes), 0.058 Ci (58 Ci/mmol) of [$^3$H]-kainate and the substances to be tested in a total of 1 ml of binding buffer. The nonspecific binding was determined in the presence of 0.1 mM glutamate. Incubation on ice for 60 min was followed by filtration through CF/B filters and subsequent washing with 5 ml of ice-cold binding buffer to separate bound and free ligand from one another. The CF/B filters had previously been treated for at least 2 h with 0.5% polyethyleneimine. Analysis of the displacement plots and calculation of the dissociation constants took place using a nonlinear fitting program or in accordance with the equation of Cheng and Prusoff.

It is possible to use the results from the following designs of tests to demonstrate the in vivo activity of the novel substances:

4. Anticonvulsant Effect (maximum electroshock in mice)

Tonic spasms of the rear limbs of mice are induced by a maximum electroshock. The occurrence of spasms can be antagonized by pretreatment with test substances. This antispasmodic effect is a pointer for the possible use of a substance as antiepileptic.

The ED 50% (=dose at which 50% of the tested animals were protected) found for N-(1(1-carboxymethyl-6-trifluoromethylquinoxaline-2,3(1H, 4H)-dion-7-yl)pyrrol-3-ylmethyl)-N'-(4-carboxyphenyl)urea (Example 4) was <46 mg/kg after i.p. administration. This means that the substance is distinctly more active than the urea derivative disclosed in Example 10 of DE-A-434 00 45.

Protection Against Cerebral Overexcitation by Excitatory Amino acids (NMDA and AMPA antagonists in vivo, mouse)

Intracerebral administration of excitatory amino acids (EAA) induces such massive overexcitation that it leads in a short time to convulsions and death of the animals. These signs can be inhibited by systemic, eg. intraperitoneal, administration of centrally acting EAA antagonists. Since excessive activation of EAA receptors in the central nervous system plays an important part in the pathogenesis of various neurological disorders, the demonstration of EAA antagonism in vivo suggests that the substances can be used therapeutically for CNS disorders of these types. These include focal and global ischemias, trauma, epilepsies and various neurodegenerative disorders such as Huntington's chorea, Parkinson's disease inter alia.

The ED50% (=dose at which 50% of the tested animals were protected) found for N-(1-(1carboxymethyl-6-trifluoromethylquinoxaline-2,3(1H,4H)-dion-7-yl)pyrrol-3-ylmethyl)-N'-(4-carboxyphenyl)urea (Example 4) was <30 mg/kg after i.p. administration. This means that the substance is distinctly more active than the urea derivatives disclosed in DE-A-4340045.

6. Therapeutic Effect on Experimental Cerebral Infarct (MCA occlusion in the rat; MCA=middle cerebral artery)

Permanent occlusion of the middle cerebral artery in rats causes experimental cerebral infarct whose extent is determined from the dead tissue after 24 hours. The volume of the cortical infarct can be reduced by the test substances even if the treatment is not started until 90 min after the vascular occlusion. Therapeutic use of the substances for human stroke can be inferred from this.

The substances according to the invention are suitable for treating all disorders in which a beneficial effect can be expected from glutamate antagonists.

Suitable indications are neurotoxic disturbances, especially acute and chronic oxygen/nutrient deficiency states of the central nervous system. These mean acute hypoxic and ischemic states which occur, for example, as a consequence of cerebral infarct, subarachnoid hemorrhage or vasospasms of other origins, and after cardiovascular breakdown, eg. in cardiac arrest, cardiac arrhythmias or circulatory shock; CNS damage after hypoglycemia, as a consequence of perinatal asphyxia and after craniocerebral trauma, spinal cord trauma, transient ischemic attacks (TIAs), prolonged reversible ischemic neurological deficits (PRINDs), multiinfarct dementia and atherosclerotic dementia, and migraine.

Other possible indications are neurodegenerative disorders, eg. Parkinson's disease, Huntington's chorea, Alzheimer's disease, amyotrophic lateral sclerosis (ALS).

Glutamate antagonists are furthermore suitable for use as antiepileptics, as anxiolytics and as antidepressants, and for the treatment of pain, as well as for the treatment of schizophrenia, of withdrawal symptoms in addicts, and as muscle relaxants when there is spasticity of skeletal muscles, eg. in multiple sclerosis (MS).

The pharmaceutical compositions according to the invention comprise a therapeutically effective amount of the compounds I besides conventional pharmaceutical ancillary substances.

The agents can be present in the usual concentrations for local external use, eg. in dusting powders and ointments. As a rule, the agents are present in an amount of from 0.0001 to 1% by weight, preferably 0.001 to 0.1% by weight.

For internal use, the preparations are administered in single doses. From 0.1 to 100 mg are given per kg of body weight in a single dose. The compositions can be administered in one or more doses each day depending on the nature and severity of the disorders.

Appropriate for the required mode of administration, the pharmaceutical compositions according to the invention comprise conventional excipients and diluents besides the agent. For local external use it is possible to use pharmaceutical ancillary substances such as ethanol, isopropanol, ethoxylated castor oil, ethoxylated hydrogenated castor oil, polyacrylic acid, polyethylene glycol, polyethylene glycol stearate, ethoxylated fatty alcohols, liquid paraffin, petroleum and lanolin. Examples suitable for internal use are lactose, propylene glycol, ethanol, starch, talc and polyvinylpyrrolidone.

It is also possible for antioxidants such as tocopherol and butylated hydroxyanisole and butylated hydroxytoluene, flavor-improving additives, stabilizers, emulsifiers and lubricants to be present.

The substances present besides the agent in the composition, and the substances used in the production of the pharmaceutical composition, are toxicologically acceptable and compatible with the particular agent. The pharmaceutical compositions are produced in a conventional way, eg. by mixing the agent with conventional excipients and diluents.

The pharmaceutical compositions can be administered in various ways, such as orally, parenterally, subcutaneously, intraperitoneally and topically. Thus, possible presentations are tablets, emulsions, infusion and injection solutions, pastes, ointments, gels, creams, lotions, dusting powders and sprays.

EXAMPLES

Example 1

N'-(4-Ethoxycarbonylphenyl)-N-(1-(6-trifluoromethylquinoxaline-2,3(1H, 4H)-dion-7-yl)-pyrrol-3-ylmethyl)urea

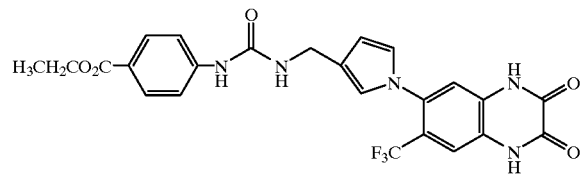

a) 7-(3-Trifluoroacetamidomethyl-1-pyrrolyl)-6-trifluoromethyl-quinoxaline-2,3(H,4H)-dione 7.0 g (32.8 mmol) of 7-amino-6-trifluoromethylquinoxaline-2,3(1H,4H)-dione, described in EP-A-572 852, and 8.5 g (33 mmol) of 2,5-dimethoxy-3-trifluoroacetamidomethyltetrahydrofuran, disclosed in WO 95/35289, were refluxed in 200 ml of glacial acetic acid for 20 minutes. After cooling, the reaction mixture was poured into water, and the resulting precipitate was filtered off with suction and washed with a large amount of water. 9.6 g (70%) of the product were obtained.

$^1$H-NMR (D$_6$-DMSO): δ=4.2 (2H), 6.2 (1H), 6.8 (2H), 7.1 (1H), 7.5 (1H), 9.9 (1H) and ca. 12,5 (broad) ppm.

b) 7-(3-Aminomethyl-1-pyrrolyl)-6-trifluoromethylquinoxaline-2,3(1H,4H)-dione 9.4 g (22.4 mmol) of the product from Example 1a were stirred with 2.1 g (89.5 mmol) of lithium hydroxide in 150 ml of water at room temperature for 1 h. The reaction mixture was then neutralized with 1 M hydrochloric acid, and the resulting precipitate was filtered off with suction. 6.7 g (93%) of the product were obtained.

1H-NMR (D$_6$-DMSO): δ=3.8 (2H), 6.2 (1H), 6.8 (1H), 6.9 (1H), 7.0 (1H) and 7.4 (1H) ppm.

c) N'-(4-Ethoxycarbonylphenyl)-N-(1-(6-trifluoromethyl-quinoxaline-2,3(1H,4H)dion-7-yl)pyrrol-3-ylmethyl)urea 2 g (6.2 mmol) of the product from Example 1b and 1.24 g (6.5 mmol) of 4-ethoxycarbonylphenyl isocyanate were stirred in 50 ml of anhydrous dimethylformamide at 50° C. for 30 minutes. The reaction mixture was then poured into 1 M hydrochloric acid and the resulting precipitate was filtered off with suction. 3.6 g (81%) of the product were obtained.

1H-NMR (D$_6$-DMSO): δ=1.3 (3H), 4.2–4.5 (4H), 6.2 (1H), 6.7(1H), 6.9 (2H), 7.1 (1H), 7.4–8.0 (5H), 9.1 (1H) and ca. 12.5 (2H) ppm.

Example 2

N'-(4-Carboxyphenyl)-N-(1-(6-trifluoromethylquinoxaline-2,3-(1H,4H) dion-7-yl)pyrrol-3-ylmethyl)urea

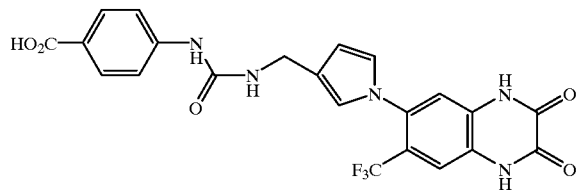

1.6 g (3.1 mmol) of the compound from Example 1 and 0.3 g (12.4 mmol) of lithium hydroxide were stirred in 40 ml of water at room temperature for 2 h. The mixture was then filtered, and the filtrate was neutralized with 1 M hydrochloric acid. The resulting precipitate was filtered off with suction. 1.1 g (74%) of the product were obtained.

1H-NMR (D$_6$-DMSO): δ=4.2 (2H), 6.2 (2H), 6.8 (2H), 7.2 (1H), 7.4–8.0 (5H), 9.5 (1H) and ca. 12,5 (broad) ppm.

Example 3

N-(1-(1-Carboxymethyl-6-trifluoromethylquinoxaline-2,3 (1H,4H)-dion-7-yl)pyrrol-3-ylmethyl)-N'-(4-ethoxycarbonylphenyl)urea

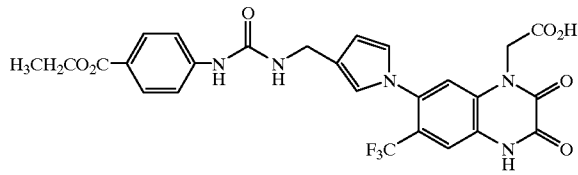

a) Ethyl N-(2-nitro-4-trifluoromethylphenyl)oxamate 51.5 g (0.25 mol) of 2-nitro-4-trifluoromethylaniline, 45 ml (0.32 mol) of triethylamine and 0.1 g of N,N-dimethylaminopyridine were dissolved in 500 ml of anhydrous tetrahydrofuran under a nitrogen atmosphere. At 0–5° C., 44.4 g (0.32 mol) of ethyl oxalyl chloride were added dropwise. The mixture was then stirred at room temperature until conversion was complete (check by thin-layer chromatography). The residue after concentration under reduced pressure was partitioned between water and ethyl acetate. The organic phase was dried and concentrated under reduced pressure. The crude product was recrystallized from ethanol to result in 68.2 g (89%) of the product.

$^1$H-NMR (CDCl$_3$): δ=1.5 (3H), 4.5 (2H), 8.0 (1H), 8.6 (1H), 9.05 (1H) and 12.2 (1H) ppm.

Ethyl N-(ethoxycarbonylmethyl)-N-(2-nitro-4-trifluoromethylphenyl)oxamate 70 g (0.23 mol) of the product from Example 3a were dissolved in 1 liter of anhydrous tetrahydrofuran under a nitrogen atmosphere. At room temperature, 34.8 g (0.31 mol) of potassium tert-butanolate were added in portions. After stirring for 30 min., 42.1 g (0.25 mol) of ethyl bromoacetate were added dropwise, and the mixture was stirred for 2 h. The reaction mixture was then concentrated under reduced pressure, and the residue was partitioned between ethyl acetate and water. The organic phase was dried and concentrated under reduced pressure. 63 g (70%) of the crude product were obtained and were immediately processed further.

c) 1-(Ethoxycarbonylmethyl)-6-trifluoromethylquinoxaline-2,3(1H,4H)-dione 63 g (0.16 mol) of the product from Example 3b were dissolved in 1 liter of acetic acid and boiled under reflux. 54 g (0.97 mol) of iron powder were added to this in portions. After heating for 1 h, the reaction mixture was cooled and filtered. The filtrate was concentrated under reduced pressure, and the residue was treated with water. The resulting solid was filtered off with suction and recrystallized from ethanol. 48.2 g (95%) of the product were obtained.

Melting point 250–251° C.

$^1$H-NMR (D$_6$-DMSO): δ=1.25 (3H), 4.7 (2H), 5.0 (2H), 7.5 (3H), and 12.4 (1H) ppm.

d) 1-(Ethoxycarbonylmethyl)-7-nitro-6-trifluoromethyl-quinoxaline-2,3(1H,4H)-dione 47 g (0.15 mol) of the product from Example 3c were dissolved in 500 ml of concentrated sulfuric acid and, at 0° C., 15 g (0.149 mol) of potassium nitrate were added in portions. The reaction mixture was stirred for a further 30 min. and then poured into ice-water. The aqueous phase was extracted with ethyl acetate, and the resulting precipitate was filtered off with suction and recrystallized from ethanol. 45.9 g (89%) of the product were obtained.

$^1$H-NMR (D$_6$-DMSO): δ=1.25 (3H), 4.2 (2H); 5.0 (2H), 7.7(1H), 8.25 (1H) and 12.7 (1H) ppm.

e) 7-Amino-1-(ethoxycarbonylmethyl)-6-trifluoromethyl-quinoxaline-2,3(1H, 4H)-dione 43 g (0.12 mol) of the product from Example 3d were dissolved in 300 ml of dimethylformamide and, after addition of 2 g of palladium/carbon (10%), hydrogenated under 1 bar at room temperature. The mixture was then filtered, and the filtrate was concentrated under reduced pressure. The residue was treated with ethanol and filtered off with suction. 37.1 g (95%) of the product were obtained.

Melting point >250° C.

$^1$H-NMR (D$_6$-DMSO): δ=1.25 (3H), 4.2 (2H), 4.85 (2H), 5.5 (2H), 6.6 (1H), 7.2 (1H) and 12.0 (1H) ppm.

f) 1-Ethoxycarbonylmethyl-7-(3-trifluoroacetamidomethyl-1-pyrrolyl)-6-trifluoromethylquinoxaline-2,3(1H,4H)-dione 4.0 g (12.1 mmol) of the product from Example 3e and 3.1 g (12.1 mmol) of the product from Example 4a were refluxed in 75 ml of glacial acetic acid for 10 min. The reaction mixture was then concentrated under reduced pressure, and the residue was treated with ethanol and filtered off with suction.

Yield: 4.8 g (79%), melting point >200° C. (decomposition)

$^1$H-NMR (D$_6$-DMSO): δ=1.2 (3H), 4.2 (2H), 4.3 (2H), 5.0 (2H), 6.2 (1H), 6.8 (2H); 7.5–7.7 (2H), 9.9 (1H) and 12.5 (1H) ppm.

g) 7-(3-Aminomethyl-1-pyrrolyl)-1-carboxymethyl-6-trifluoromethylquinoxaline-2,3(1H,4H)-dione 4.7 g (9.3 mmol) of the product from Example 3f were added to 50 ml of tetrahydrofuran, and 75 ml of a 0.5 M lithium hydroxide solution were added. The mixture was stirred at room temperature for 1 h. The tetrahydrofuran was subsequently removed under reduced pressure, and the resulting aqueous phase was neutralized with 1M hydrochloric acid. The resulting precipitate was filtered off with suction.

Yield: 3.3 g (94%), melting point >250° C.

$^1$H-NMR (CD$_3$COOD): δ=4.2 (2H), 5.0 (2H), 6.45 (1H), 6.95 (1H), 7.1 (1H), 7.4 (1H) and 7.8 (1H) ppm.

h) N-(1-(1-Carboxymethyl-6-trifluoromethylquinoxaline-2,3(1H,4H)-dion-7-yl)pyrrol-3-ylmethyl)-N'-(4-ethoxycarbonylphenyl)urea 2 g (5.2 mmol) of the product from Example 3g and 1.1 g (5.8 mmol) of 4-ethoxycarbonylphenyl isocyanate were heated in 30 ml of anhydrous dimethylformamide at 505C. for 5 minutes. The reaction mixture was then added to 1M hydrochloric acid, and the precipitate was filtered off with suction. 1.8 g (69%) of the product were obtained.

$^1$H-NMR (D$_6$-DMSO): δ=1.3 (3H), 4.1–4.4 (4H), 5.0 (2H), 6.2 (1H), 6.5 (1H), 6.9 (2H), 7.4–8.0 (6H), 8.9 (1H) and 12.5 (1H) ppm.

Example 4

N-(1-Carboxymethyl-6-trifluoromethylquinoxaline-2,3(1H,4H)-dion-7-yl) pyrrol-3-ylmethyl)-N'-(4-carboxyphenyl)urea

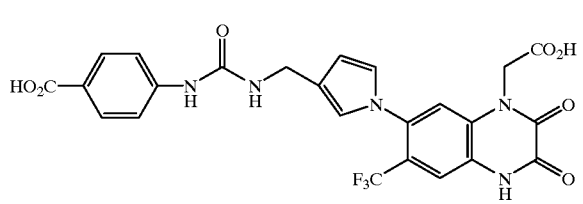

1.2 g (2.1 mmol) of the compound from Example 3 and 0.2 g (8.6 mmrol) of lithium hydroxide were reacted by the method of Example 2. 1.0 g (87%) of the product was obtained.

$^1$H-NMR (D$_6$-DMSO): δ=4.2 (2H), 4.9 (2H), 6.2 (1H), 6.5 (1H), 6.9 (2H), 7.4–7.9 (6H), 8.9 (1H) and ca. 12.5 (2H) ppm.

Example 5

N-(1-(1-Carboxymethyl-6-trifluoromethylquinoxaline-2,3(1H,4H)-dion-7-yl)pyrrol-3-ylmethyl)-N'-(3-ethoxycarbonylphenyl)urea

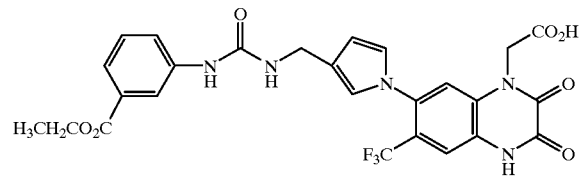

2 g (5.2 mmol) of the product from Example 3g and 1.1 g (5.8 mmol) of 3-ethoxycarbonylphenyl isocyanate were reacted by the method of Example 3h to result in 1.7 g (66%) of the product.

$^1$H-NMR (D$_6$-DMSO): δ=1.3 (2H), 4.2 (2H), 4.3 (2H), 4.9 (2H), 6.2 (1H), 6.4 (1H), 6.9 (2H), 7.3–7.8 (5H), 8.1 (1H), 8.7 (1H), 12.5 (1H) and ca. 13 (broad) ppm.

Example 6

N-(1-Carboxymethyl-6-trifluoromethylquinoxaline-2,3(1H,4H)-dion-7-yl)pyrrol-3-ylmethyl)-N'-(3-carboxyphenyl)urea

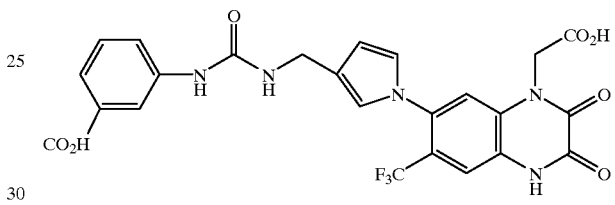

1.1 g (2 mmol) of the compound from Example 5 and 0.19 g (7.8 mmol) of lithium hydroxide were reacted via the method of Example 4 to result in 0.9 g (82%) of the product.

$^1$H-NMR (D$_6$-DMSO): δ=4.2 (2H), 5.0 (2H), 6.2 (1H), 6.3(1H), 6.9 (2H); 7.2–7.7 (5H), 8.0 (1H), 8.7 (1H), 12.5 (1H) and ca. 13 (broad) ppm.

Example 7

N'-(4-Ethoxycarbonylphenyl)-N-(1-(1-(2-hydroxyethyl)-6-trifluoromethylquinoxaline-2,3(1H,4H)-dion-7-yl)pyrrol-3-ylmethyl)urea

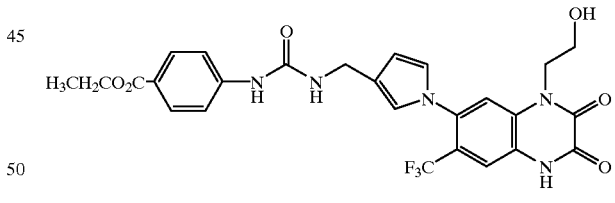

a) 4-(2-Hydroxyethylamino)-3-nitrobenzotrifluoride 112.8 g (0.5 mol) of 4-chloro-3-nitrobenzotrifluoride and 61.1 g (1 mol) of 2-ethanolamine were heated in 50 ml of dimethylformamide at 100° C. for 2 h. The reaction mixture was then concentrated under reduced pressure, and water was added to the residue. The precipitate was filtered off with suction and recrystallized from cyclohexane.

Yield: 116 g (46%), melting point 68–70° C.

$^1$H-NMR (D$_6$-DMSO): δ=3.5 (2H), 3.7 (2H), 5.0(1H), 7.3 (1H), 7.8 (1H), 8.3 (1H) and 8.6 (1H) ppm.

b) 3-Amino-4-(2-hydroxyethylamino)benzotrifluoride 115 g (0.46 mol) of the product from Example 7a were dissolved in 1 liter of isopropanol, 11.5 g of palladium/carbon (10%) in 200 ml of water were added, and the mixture was heated to 80° C. Then 91 g (1.4 mol) of ammonium formate dissolved in 175 ml of water were rapidly added dropwise. After the reaction was complete, the mixture was filtered, and the alcohol was removed from the filtrate under reduced pressure. The resulting precipitate was filtered off with suction, treated with toluene and again filtered off with suction.

Yield: 68.4 g (68%), melting point 92–94° C.

$^1$H-NMR (D$_6$-DMSO): δ=3.2 (2H), 3.6 (2H), 4.8 (1H), 4.9 (2H), 5.1 (1H), 6.5 (1H), and 8.6 (2H) ppm.

c) 1-(2-Hydroxyethyl)-6-trifluoromethylquinoxaline-2,3 (1H,4H)-dione 60 g (0.27 mol) of the product from Example 7b were refluxed in 500 ml of ethyl oxalate for 3 h. After cooling, the precipitate was filtered off with suction.

Yield: 55 g (74%), melting point 275–276° C.

$^1$H-NMR (D$_6$-DMSO): δ=3.7 (2H), 4.2 (2H), 4.9 (1H), 7.4 (1H) and 12.2 (1H) ppm.

d) 1-(2-Hydroxyethyl)-7-nitro-6-trifluoromethylquinoxaline-2,3(1H,4H)-dione 50 g (0.18 mol) of the product from Example 7c were dissolved in 500 ml of concentrated sulfuric acid and, at 0° C., 21 g (0.21 mol) of potassium nitrate were added in portions. The mixture was then stirred for 30 min. The reaction mixture was subsequently poured onto ice, and the precipitate was filtered off with suction.

Yield: 25 g (44%), melting point 254–256° C.

$^1$H-NMR (D$_6$-DMSO): δ=3.6 (2H), 4.1 (2H), 4.5 (1H); 7.6 (1H); 8.3 (1H) and ca. 12 (broad) ppm.

e) 7-Amino-1-(2-hydroxyethyl)-6-trifluoromethylquinoxaline-2,3 (1H,4H)-dione 25 g (78 mmol) of the product from Example 7d were reduced with 50 g (0.79 mol) of ammonium formate as in method 7d.

Yield: 13.2 g (58%), melting point 278° C. (decomposition)

$^1$H-NMR (D$_6$-DMSO): δ=3.6 (2H), 4.1 (H), 4.4 (broad), 5.5 (2H), 6.9 (1H), 7.1 (1H) and 11.8 (broad) ppm.

f) N-(2,5-Dimethoxy-3-tetrahydrofuranylmethyl)-N'-(4-ethoxycarbonylphenyl)urea 2.9 g (18 mmol) of 3-aminomethyl-2,5-dimethoxytetrahydrofuran (DE-A 26 45 234) were dissolved in 20 ml of anhydrous tetrahydrofuran. At 0° C., 2.9 g (15 mmol) of 4-ethoxycarbonylphenyl isocyanate dissolved in 10 ml of anhydrous tetrahydrofuran were added dropwise. The mixture was then stirred at room temperature for 1 h and then concentrated under reduced pressure, resulting in 5.5 g of the crude product.

$^1$H-NMR (CDCl$_3$): δ=1.4 (3H), 3.2–3.6 (8H), 4.4 (2H), 4.8–5.2 (2H), 5.9 (1H), 7.4 (2H) and 7,9 (2H) ppm.

g) N'-(4-Ethoxycarbonylphenyl)-N-(1(1-(2-hydroxyethyl)-6-trifluoromethylquinoxaline-2,3(1H,4H)-dion-7-yl)pyrrol-3-yl-methyl)urea 2.5 g (8.7 mmol) of the product from Example 7e and 3.4 g (9.6 mmol) of the product from Example 7f were refluxed in 50 ml of glacial acetic acid for 15 minutes. The mixture was then poured into water, and the precipitate was filtered off with suction and then purified by chromatography on silica gel with the eluent toluene/acetone/glacial acetic acid= 30/20/1, resulting in 1.0 g (22%) of the product.

$^1$H-NMR (D$_6$-DMSO): δ=1.3 (3H), 4.2–4.6 (8H), 6.2 (1H); 6.5 (1H), 6.9 (2H), 7.4–8.0 (6H), 8.9 (1H) and ca. 12.5 (broad) ppm.

Example 8

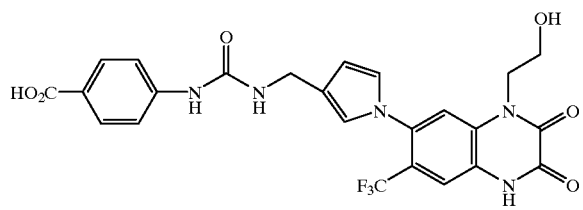

N'-(4-Carboxyphenyl)-N-(1-(1-(2-hydroxyethyl)-6-trifluoromethylquinoxaline-2,3(1H,4H)-dion-7-yl)pyrrol-3-ylmethyl)urea 0.66 g (1.2 mmol) of the compound from Example 7 and 0.14 g (8.6 mmol) of lithium hydroxide were reacted via the method of Example 4, resulting in 0.6 g (89%) of the product.

$^1$H-NMR (D$_6$-DMSO): δ=3.7 (2H), 4.2 (4H), 4.9 (1H), 6.2 (1H), 6.5 (1H), 6.9 (2H), 7.4–8.0 (6H), 8.9 (1H), 12.3 (1H) and ca. 12.5 (broad) ppm.

We claim:

1. A pyrrolidylquinoxalinedione of the formula I

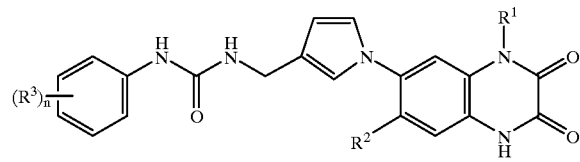

or its tautomeric form or its physiologically tolerated salt, wherein $R^1$ is hydrogen, $C_1$–$C_6$-alkyl, substituted by hydroxyl or carboxyl, $R^2$ is hydrogen, $C_1$–$C_6$-alkyl, $C_2$–$C_6$-alkenyl, $C_2$–$C_6$-alkynyl, a chlorine, fluorine or bromine atom, a trihalomethyl, cyano or nitro group or $SO_2$—$C_1$–$C_4$-alkyl, $R^3$ is COOH or a radical which can be hydrolyzed to the carboxyl group selected from the group consisting of an amide group $CONH_2$ and an ester group $COOR^4$ wherein $R^4$ is $C_1$–$C_4$-alkyl, or, in the event that n is 2 and the radicals $R^3$ are bonded to adjacent carbon atoms of the phenyl ring, said radicals $R^3$ additionally represent a —CO—O—CO— moiety, n is 1 or 2.

2. The pyrrolidylquinoxalinedione defined in claim 1, wherein $R^1$ is hydrogen, $R^2$ is hydrogen, chlorine, a trifluoromethyl or nitro group, $R^3$ is COOH.

3. The pyrrolidylquinoxalinedione defined in claim 1, wherein $R^1$ is —CH$_2$COOH or —CH$_2$CH$_2$OH, $R^2$ is hydrogen, chlorine, a trifluoromethyl or nitro group, $R^3$ is COOH.

4. A method of producing a drug for the treatment of a disease or disorder in which there is an elevated glutamate activity in the central nervous system, which disease or disorder is selected from the group consisting of epilepsy, ischemia, hypoxia and anoxia, or for the treatment of Parkinson's Desease or for use as a muscle relaxant which method comprises admixing an effective amount of the pyrrolidylquinoxalinedione defined in claim 1 with at least one conventional pharmaceutical ancillary substance.

5. A pharmaceutical composition for oral, parenteral and intraperitoneal use, comprising from 0.1 to 100 mg of at least one pyrrolylquinoxalinedione I as claimed in claim 1 per kg of body weight per single dose, besides conventional pharmaceutical ancillary substances.

6. A pharmaceutical composition for intravenous use, comprising from 0.0001 to 10% by weight of at least one pyrrolylquinoxalinedione I as claimed in claim 1, besides conventional pharmaceutical ancillary substances.

7. A method of treating a disease or disorder in which there is an elevated glutamate activity in the central nervous system of a patient, which disease or disorder is selected from the group consisting of epilepsy, ischemia, hypoxia and anoxia, which method comprises administering an effective amount of the pyrrolidylquinoxalinedione defined in claim 1 to the patient.

8. A method of treating Parkinson's disease in a patient which comprises administering an effective amount of the pyrrolidylquinoxalinedione defined in claim 1 to the patient.

9. A method of treating spasticity of skeletal muscles in a patient which comprises administering an effective amount of the pyrrolidylquinoxalinedione defined in claim 1 to the patient.

* * * * *